US009687158B2

(12) United States Patent
Watanabe

(10) Patent No.: US 9,687,158 B2
(45) Date of Patent: Jun. 27, 2017

(54) FLUORESCENCE OBSERVATION APPARATUS

(71) Applicant: OLYMPUS CORPORATION, Tokyo (JP)

(72) Inventor: Toshiaki Watanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 462 days.

(21) Appl. No.: 14/242,111

(22) Filed: Apr. 1, 2014

(65) Prior Publication Data

US 2014/0213871 A1 Jul. 31, 2014

Related U.S. Application Data

(63) Continuation of application No. PCT/JP2012/074560, filed on Sep. 25, 2012.

(30) Foreign Application Priority Data

Oct. 6, 2011 (JP) .................................. 2011-222153

(51) Int. Cl.
A61B 5/00 (2006.01)
A61B 5/02 (2006.01)
A61B 1/04 (2006.01)

(52) U.S. Cl.
CPC .......... *A61B 5/02042* (2013.01); *A61B 1/043* (2013.01)

(58) Field of Classification Search
CPC ........................... A61B 5/02042; A61B 1/043
See application file for complete search history.

(56) References Cited

U.S. PATENT DOCUMENTS

2002/0138008 A1* 9/2002 Tsujita ............... A61B 1/00009
600/473
2002/0177779 A1* 11/2002 Adler ................. A61B 1/00009
600/476

(Continued)

FOREIGN PATENT DOCUMENTS

JP 2001017387 A 1/2001
JP 2006095166 A 4/2006

(Continued)

OTHER PUBLICATIONS

International Search Report dated Oct. 30, 2012 received in corresponding International Application No. PCT/JP2012/074560.

*Primary Examiner* — Tiffany Weston
(74) *Attorney, Agent, or Firm* — Scully, Scott, Murphy & Presser, PC

(57) ABSTRACT

Provided is a fluorescence observation apparatus including a light source; a section generating a fluorescence image of an object; a section generating a reference image of the object; a section generating a corrected image in which emphasized are pixels of the reference image corresponding to pixels each having luminance value equal to or more than a first threshold value in the fluorescence image; a display unit displaying the reference image or the corrected image; a bleeding state determining section determining whether or not a bleeding region of the subject detected based on the reference image is more than a predetermined range; and a section switching between displaying the reference image on the display unit if the determining section determines that the region is not more than the range, and displaying the corrected on the image display if the determining section determines that the region is more than the range.

3 Claims, 7 Drawing Sheets

(56) References Cited

U.S. PATENT DOCUMENTS

2005/0059894 A1* 3/2005 Zeng ................ A61B 1/00055
600/476
2010/0182412 A1* 7/2010 Taniguchi ............ A61B 1/041
348/65

FOREIGN PATENT DOCUMENTS

JP   2008086605 A   4/2008
WO  2011080996 A1  7/2011

* cited by examiner

FLUORESCENCE OBSERVATION APPARATUS

TECHNICAL FIELD

The present invention related to a fluorescence observation apparatus.

BACKGROUND ART

Recently, so-called endoscopic surgery have been widely practiced in which a lesion is treated using predetermined treatment tools while monitoring images on the lesion obtained through an endoscopic device. Patent Literature 1 describes an endoscopic device or an endoscope observation system for use in such endoscopic surgery.

CITATION LIST

Patent Literature

{PTL 1}
Japanese Unexamined Patent Application, Publication No. 2001-17387

SUMMARY OF INVENTION

Solution to Problem

In order to solve the above problems, the present invention employs the following solution.

One aspect of the present invention provides a fluorescence observation apparatus including: a light source for radiating excitation light and reference light onto a subject; a fluorescence image generating section that generates a fluorescence image by capturing fluorescence generated at the subject due to the irradiation with the light source; a reference image generating section for photographing optical feedback returning from the subject irradiated with the reference light from the light source so as to generate a reference image; a corrected image generating section for generating a corrected image in which emphasized are pixels of the reference image corresponding to pixels each having luminance value equal to or more than a first threshold value in the fluorescence image; an image display unit for displaying the reference image or the corrected image; a bleeding state determining section for detecting a bleeding region of the subject based on the reference image, and determining whether or not the bleeding region is more than a predetermined range; and a display image switching section for switching between displaying the reference image on the image display unit if the bleeding determining section determines that the bleeding region is not more than the predetermined range, and displaying the corrected image on the image display unit if the bleeding determining section determines that the bleeding region is more than the predetermined range.

DESCRIPTION OF EMBODIMENTS

First Embodiment

Figure 1:
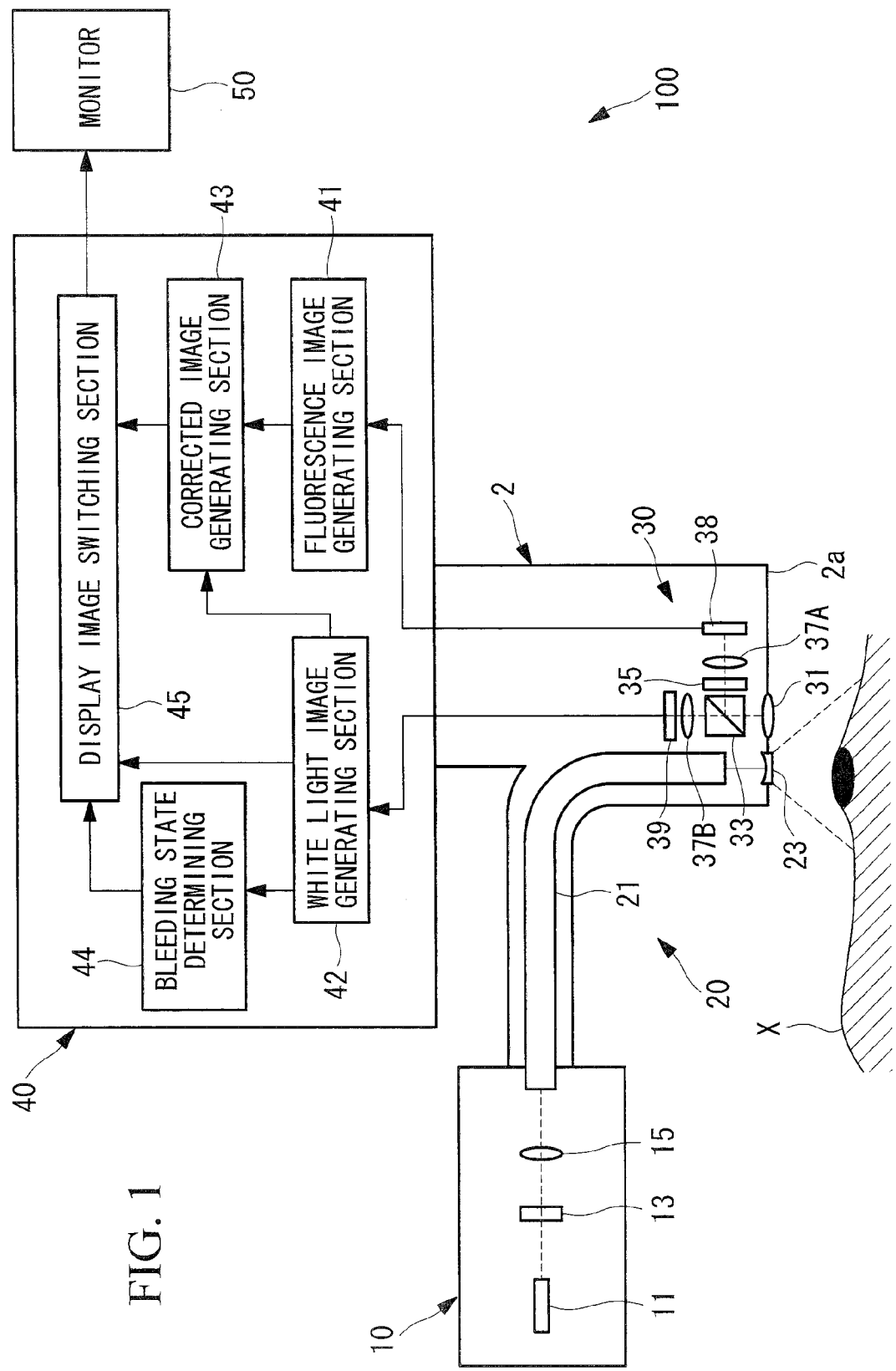
FIG. 1 is a schematic diagram of an endoscopic device according to the first embodiment of the present invention.

The first embodiment of the present invention will be described with reference to drawings, hereinafter.

An endoscopic device 100 as a fluorescence observation apparatus according to the present embodiment includes: a long scope 2 to be inserted in a body cavity; an illumination unit 20 including a light source 10 emitting illumination light from a front end 2a of the scope 2; a photographing unit 30 so disposed in the scope 2 as to acquire image information regarding a treatment site X that is a subject; an image processing unit 40 for processing the image information acquired by the photographing unit 30; and a monitor (image display unit) 50 for displaying an image and image information, etc., processed by the image processing unit 40.

The light source 10 includes: a xenon lamp (Xe lamp) 11 for emitting the illumination light; an excitation light filter 13 for cutting off white light including excitation light from the illumination light emitted from the xenon lamp 11; and a coupling lens 15 for condensing the white light including the excitation light cut off by the excitation light filter 13. The excitation light filter 13 is configured to cut off the white light including the excitation light having a wavelength bandwidth of 400 to 740 nm.

The illumination unit 20 includes: a light guide fiber 21 disposed substantially across the entire longitudinal length of the scope 2; and a diffusing lens 23 disposed at the front end 2a of the scope 2.

The light guide fiber 21 leads the white light including the excitation light condensed by the coupling lens 15 to the front end 2a of the scope 2. The diffusing lens 23 disperses and radiates the white light including the excitation light led by the light guide fiber 21 onto the treatment site X.

The photographing unit 30 includes an objective lens 31 for condensing optical feedback returning from the treatment site X to which the white light including the excitation light is radiated from the illumination unit 20, and a beam splitter 33 splits the optical feedback condensed by the objective lens 31 into individual wavelengths.

The objective lens 31 is disposed at the front end 2a of the scope 2 in parallel with the diffusing lens 23. In the optical feedback, the beam splitter 33 reflects light having a wavelength equal to or more than an excitation wavelength (excitation light and fluorescence), and transmits the white light having a wavelength shorter than the excitation wavelength (optical feedback).

The photographing unit 30 includes: an excitation light cut-off filter 35 that blocks the excitation light and transmits only fluorescence (e.g. near-infrared fluorescence) in the excitation light and the fluorescence that are reflected by the beam splitter 33; a condenser lens 37A for condensing the fluorescence transmitted through the excitation light cut-off filter 35, and a condenser lens 37B for condensing the white light transmitted through the beam splitter 33; a fluorescence photographing section 38 for photographing the fluorescence condensed by the condenser lens 37A, and a white light photographing section 39 for photographing the white light condensed by the condenser lens 37B.

The excitation light cut-off filter 35 transmits only fluorescence whose wavelength bandwidth is 765 to 850 nm, for example. The fluorescence photographing section 38 may be a high sensitive monochrome CCD used for fluorescence, for example, and this fluorescence photographing section 38 acquires fluorescence image information by photographing fluorescence. The white light photographing section 39 may be a color CCD used for white light, and includes a mosaic filter (not shown). The white light photographing section 39 acquires white light image information by photographing white light.

The image processing unit 40 includes a fluorescence image generating section 41 for generating a fluorescence image; a white light image generating section (reference image generating section) 42 for generating a white light image (reference image); a corrected image generating section 43 for correcting the white light image generated by the white light image generating section 42 so as to generate the corrected image; and a bleeding state determining section 44 for determining a bleeding state of the treatment site X based on the white light image; and a display image switching section 45 for switching an image to be displayed on the monitor 50 based on the determination result of the bleeding state determining section 44.

The fluorescence image generating section 41 generates a two-dimensional fluorescence image based on the fluorescence image information acquired by the fluorescence photographing section 38, and outputs the generated fluorescence image to the corrected image generating section 43.

Figure 2:
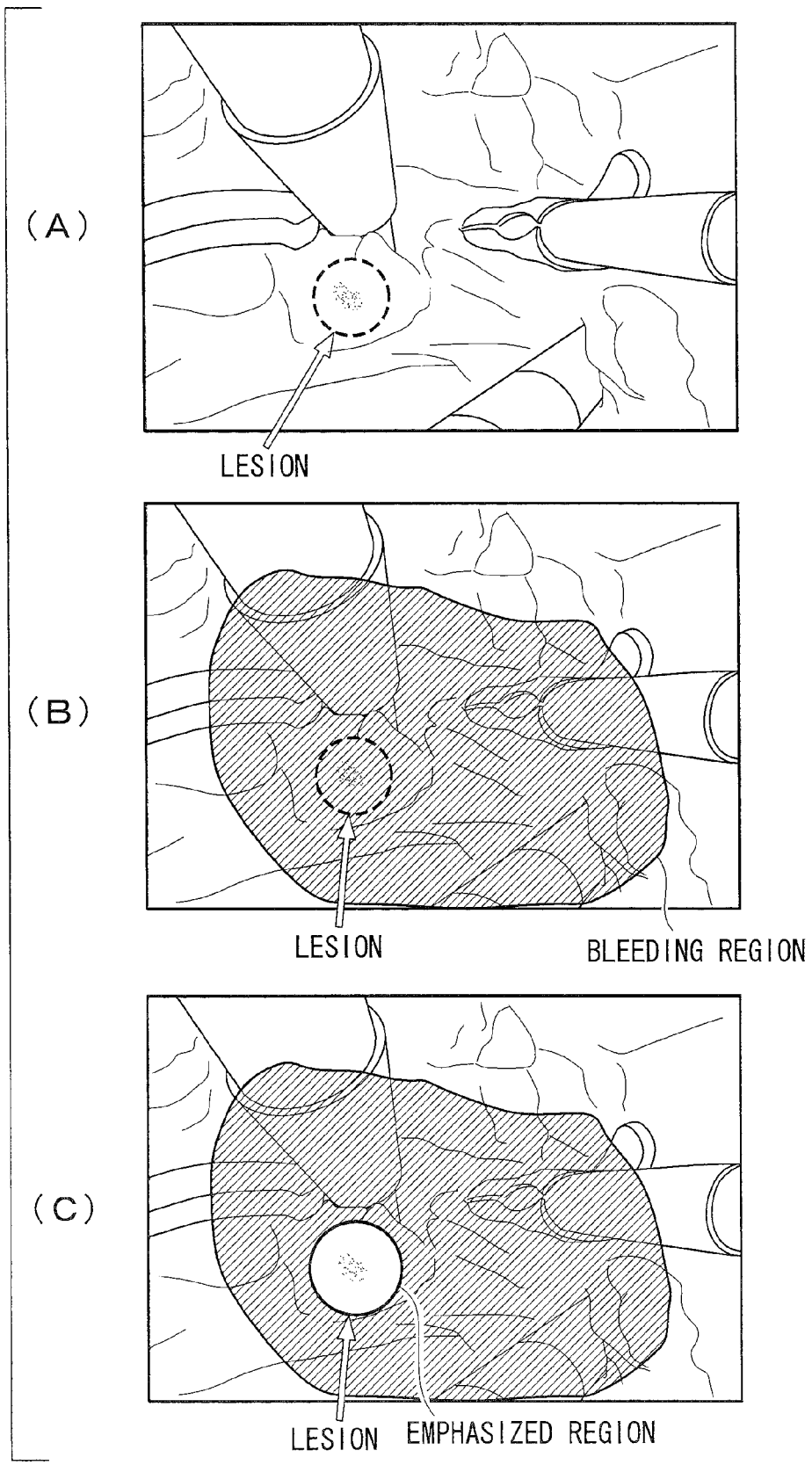
FIG. 2 is a drawing of explaining a white light image and a corrected image that are generated in the endoscopic device according to the first embodiment of the present invention.

The white light image generating section 42 generates a two-dimensional white light image based on the white light image information acquired by the white light photographing section 39, and outputs the generated white light image to the corrected image generating section 43, to the bleeding state determining section 44, and to the display image switching section 45. FIG. 2(A) shows an example of the white light image of the treatment site X, and FIG. 2(B) shows an example of the white light image if bleeding occurs in the treatment site X.

The corrected image generating section 43 generates a corrected image in which pixels of the white light image corresponding to pixels each having luminance value equal to or more than a first threshold value in the fluorescence image are emphasized. Specifically, the corrected image generating section 43 generates the corrected image where emphasized are pixels of the white light image corresponding to pixels each having high luminance value due to strong fluorescence emitted from the lesion and others in the treatment site X. FIG. 2(C) shows an example of the corrected image.

Specifically, the corrected image is generated by the corrected image generating section 43 in the following manner. The corrected image generating section 43 compares the signal value of each pixel of the fluorescence image to a predefined first threshold value, extracts pixels of the fluorescence each having luminance value equal to or more than the first threshold value, and defines a region constituted by pixels of the white light image corresponding to the pixels of the fluorescence each having luminance value equal to or more than the first threshold value as a correction target region.

For example, a signal value (e.g. constant factor of a luminance value) of each corresponding pixel of the fluorescence image is added to a G channel of each pixel constituting the correction target region of the white light image, as represented by the following formula:

$$Og(i) = Wg(i) + \alpha F(i)$$

$$Or(i) = Wr(i)$$

$$Ob(i) = Wb(i)$$

where $\alpha$ represents a predefined constant, Or(i), Og(i), and Ob(i) represent respective signal values of the R, G, and B channels in the i-th pixel of the corrected image, Wr(i), Wg(i), and Wb(i) represent respective signal values of the R, G, and B channels in the i-th pixel of the white light image, and F(i) represents a signal value in the i-th pixel of the fluorescence image.

In this manner, a certain color signal (e.g. G channel) of pixels within the correction target region is emphasized by adding to each of these pixels a signal value based on the luminance value of each corresponding pixel of the fluorescence image so as to generate the corrected image in which the concerned pixels are emphasized, that is, the correction target region is emphasized.

The bleeding state determining section 44 detects a bleeding region of the treatment site X based on the white light image inputted from the white light image generating section 42, determines whether or not the bleeding region is more than a predetermined range, and outputs the determination result to the display image switching section 45. Specifically, the bleeding state determining section 44 extracts pixels each having a signal value of the R channel more than a threshold value A from the all pixels included in the white light image, and if a signal value of the G channel relative to a signal value of the R channel of the extracted pixel of interest is smaller than a threshold value B, the bleeding state determining section 44 defines this pixel as a bleeding pixel, and then detects a region constituted by these pixels as the bleeding region.

If the detected bleeding region is more than the predetermined range, that is, if the total number of the bleeding pixels are more than a predetermined threshold value C, it is determined that the bleeding region is so great that the bleeding state occurs. If it is determined that the bleeding region is not more than the predetermined range, that is, if the total number of the bleeding pixels are less than the threshold value C, it is determined that the bleeding region is so small that no bleeding state occurs.

Based on the determination result of the bleeding state determining section 44, if it is determined that the bleeding region is not more than the predetermined range, that is, if it is determined that no bleeding state occurs, the display image switching section 45 displays the white light image on the monitor 50; and it is determined that the bleeding region is more than the predetermined range, that is, if it is determined that the bleeding state occurs, the display image switching section 45 switches from the current image to the corrected image on the monitor 50.

Figure 3:
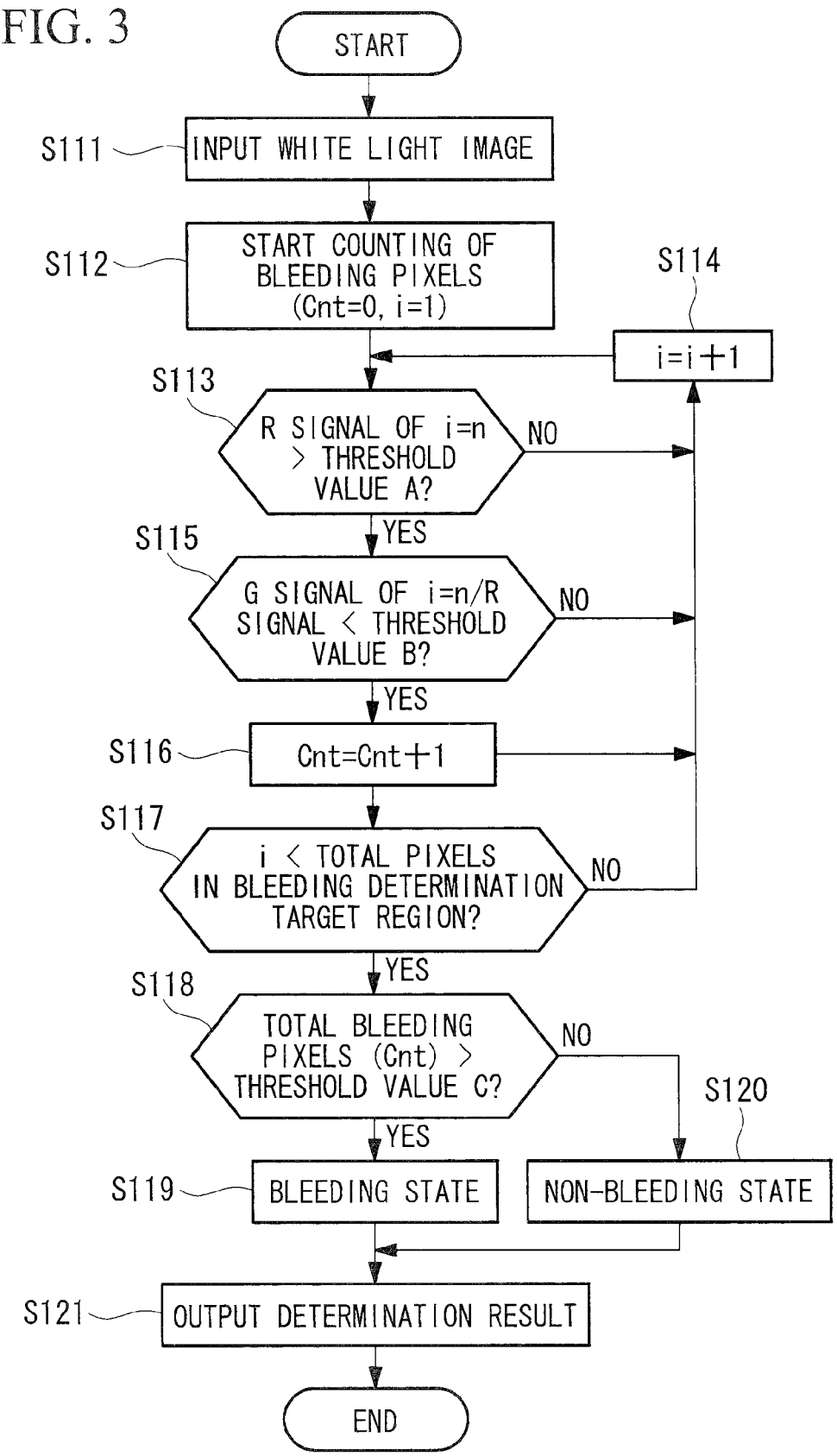
FIG. 3 is a flow chart of determining a bleeding state in the endoscopic device according to the first embodiment of the present invention.

With reference to the flow chart of FIG. 3, description will be provided on a flow of determining whether or not the treatment site X is bleeding, that is, a flow of how the bleeding state determining section 44 determines the bleeding state when desired treatment (surgery) is applied to the treatment site X in the body cavity using the endoscopic device 100 having the above configuration according to the present embodiment.

The bleeding state determining section 44 receives an input of the white light image generated by the white light image generating section 42, and starts counting of the number of the bleeding pixels in the white light image in the subsequent step S112. Specifically, in step S112, the bleeding state determining section 44 determines whether or not each of the all pixels in the white light image is a bleeding pixel, and starts calculation of the total number of the bleeding pixels. At the time of starting this calculation, the total number of the bleeding pixels is Cnt=0, and the determination regarding the bleeding pixel is carried out on every pixel of the white light image one by one from the first pixel (i=1), which is defined in advance in the white light image. The bleeding state determining section 44 calculates the total number of the bleeding pixels in step S112 to step S117, thereby detecting the bleeding region in the surgical region.

In step S113, from the first pixel, every signal value of the R channel (referred to as a "R signal", hereinafter) is compared one by one to the predetermined threshold value A, and if the R signal of interest is less than the threshold value A, it is determined that this pixel is not corresponding to the bleeding state, and then the process proceeds to step S114 so as to carry out the determination regarding the bleeding pixel on a next pixel. This is because blood is red, and if the pixel of interest has a small R signal value, it may be determined that no red color is detected, and this is not corresponding to the bleeding state. On the other hand, if it is determined that the pixel of interest is more than the predetermined threshold value A, it is considered that the pixel of interest has possibility to be corresponding to the bleeding state, and the process proceeds to the next step S115.

In next step S115, the signal value of the G channel relative to the R signal value of the pixel of interest, that is, a G signal/R signal value is compared to the predetermined threshold value B, and if the G signal/R signal value is more than the threshold vale B, it is determine that the pixel of interest is not corresponding to the bleeding state, and the process proceeds to step S114 for carrying out the determination regarding the bleeding state on a next pixel. On the other hand, if the G signal/R signal value is less than the threshold value B, it is determine that the pixel of interest is corresponding to the bleeding state, and the process proceeds to step S116. This is because, if the pixel of interest is corresponding to the bleeding state, this pixel has a higher R signal value, so that the G signal value or the B signal value becomes smaller because the G signal or the B signal is absorbed; thus the G signal/R signal becomes small. Accordingly, it can be determined that the pixel of interest is corresponding to the bleeding state if the G signal/R signal is small.

In the next step S116, the total number of the bleeding pixels that have been determined as the bleeding pixels in step S115 is added up. In step S117, based on comparison of the total number of the pixels of the white light image to the number of the pixels that have been subjected to the bleeding pixel determination, it is determined whether or not the determination regarding the bleeding pixel has been applied to the all pixels of the white light image. Based on the result, if the bleeding pixel determination has not been applied to the all pixels yet, the process proceeds to step S114 for carrying out the bleeding pixel determination on a next pixel.

Based on the determination result, if the bleeding pixel determination is carried out on the all pixels, the process proceeds to step S118. In step S118, the bleeding region in the surgical region, which has been detected by calculating the total number of the bleeding pixels in step S112 to step S117, is compared to a predetermined threshold value C so as to carry out the determination regarding bleeding state in the surgical region. In step S118, the bleeding state determining section 44 compares the total number (Cnt) of the bleeding pixels that have been added up until the current time point to the predetermined threshold value C, and if the total number of the bleeding pixels is more than the threshold value C, which means that the bleeding region is large, the process proceeds to step S119 for determining that the bleeding state occurs. If the total number of the bleeding pixels is equal to or less than the threshold value C, which means that the bleeding region is small, the process proceeds to step S120 for determining that no bleeding state occurs. In step S121, the bleeding state determining section 44 outputs one of the determination results: the bleeding state and the non-bleeding state to the display image switching section 45.

Figure 4:
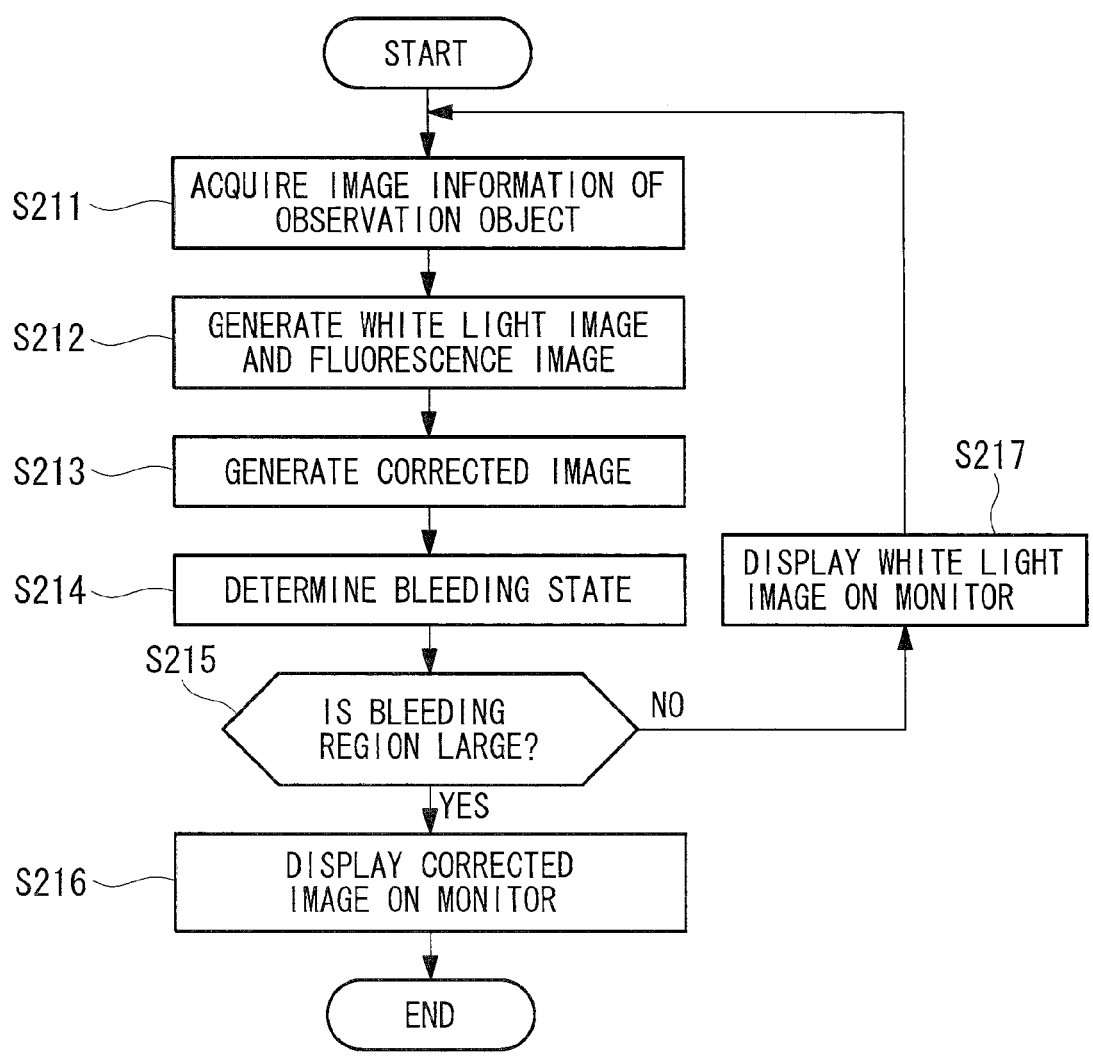
FIG. 4 is a flow chart showing an operation of the endoscopic device according to a variation of the first embodiment of the present invention.

With reference to the flow chart of FIG. 4, description will be provided on a flow of applying desired treatment (surgery) to the treatment site X in the body cavity using the endoscopic device 100 having the above configuration according to the present embodiment.

At the time of performing surgery on the treatment site X in the body cavity of a living body using the endoscopic device 100, a fluorescence agent that is specifically accumulated in the lesion, such as cancer cells, is applied or absorbed into the treatment site X, and thereafter, image information regarding the treatment site X is acquired (step S211). Specifically, in a state in which the fluorescence agent is applied or absorbed into the treatment site X, the treatment site X is irradiated with the excitation light, thereby exciting the fluorescence agent to emit fluorescence from the treatment site X.

More specifically, in the present embodiment, in a state in which the fluorescence agent is applied or absorbed into the treatment site X, the scope 2 is inserted in the body cavity, and the front end 2a thereof is set to oppose the treatment site X. In this state, if the light source 10 is operated, the white light including the excitation light is emitted from the xenon lamp 11, is cut out by the excitation light filter 13, is condensed by the coupling lens 15, and is then led to the front end 2a of the scope 2 through the light guide fiber 21. This white light is diffused by the diffusing lens 23, and is radiated onto the treatment site X.

In the treatment site X, the fluorescence material included thereinside is excited by the excitation light to emit the fluorescence, and part of the white light and the excitation light reflects on its surface. The fluorescence, the white light, and the excitation light are concentrated by the objective lens 31, and light whose wavelength is equal to or more than the excitation wavelength, that is, the excitation light and the fluorescence are reflected by the beam splitter 33, but the white light whose wavelength is less than the excitation wavelength is transmitted through the beam splitter 33.

Of the excitation light and the fluorescence reflected by the beam splitter 33, the excitation light is removed by the excitation light cut-off filter 35, and only the fluorescence is concentrated by the condenser lens 37A, and is photographed by the fluorescence photographing section 38. In this manner, the fluorescence image information of the treatment site X is acquired by the fluorescence photographing section 38. The white light transmitted through the beam splitter 33 is condensed by the condenser lens 37B, and is photographed by the white light photographing section 39. In this manner, the white light image information of the treatment site X is acquired by the white light photographing section 39. Either of the fluorescence image information and the white light image information may be acquired ahead of the other, or they may be acquired at the same time.

In step S212, the fluorescence image information acquired by the fluorescence photographing section 38, and the white light image information acquired by the white light image photographing section 39 are respectively inputted into the fluorescence image generating section 41, and into the white light image generating section 42 of the image processing unit 40. The fluorescence image generating section 41 generates a two-dimensional fluorescence image based on the fluorescence image information, and outputs the generated fluorescence image to the corrected image generating section 43. The white light image generating section 42 generates a two-dimensional white light image based on the white light image information, and respectively outputs the generated white light image to the corrected image generating section 43, to the bleeding state determining section 44, and to the display image switching section 45.

In step S213, the corrected image generating section 43 generates the corrected image. Specifically, the corrected image generating section 43 compares the signal value of each pixel of the fluorescence image to the predefined first threshold value, and extracts pixels each having luminance value equal to or more than this predefined first threshold value; and thereafter, the corrected image generating section 43 adds to the G channel of the pixels of the white light image corresponding to the pixels each having luminance value equal to or more than the first threshold value of the fluorescence image a constant factor of the luminance value of each of the corresponding pixels in the fluorescence image so as to generate a corrected image, and outputs the corrected image to the display image switching section 45.

Subsequently, in step S214, the bleeding state determining section 44 determines the bleeding state of the treatment site X as described above, and outputs the determination result to the display image switching section 45. In step S215, the display image switching section 45 switches the image depending on the determination result of the bleeding state determining section 44. Specifically, in step S215, it is determined what kind of determination result of the bleeding state is inputted to the display image switching section 45, and if the determination result of the non-bleeding state is inputted, the process proceeds to step S217, and if the determination result of the bleeding state is inputted, the process proceeds to step S216.

In step S217, because no bleeding state occurs, the white light image is displayed on the monitor 50, and the process returns to step S211 for acquiring next image information. In step S216, because the bleeding state occurs, the corrected image is displayed on the monitor 50.

As aforementioned, according to the endoscopic device 100 of the present embodiment, the endoscopic device 100 detects the bleeding region, and determines the treatment site is in the bleeding state if the bleeding region exceeds the predetermined range, emphasizes the pixels each having luminance value equal to or more than the first threshold value in the white light, thereby displaying on the monitor the corrected image in which tissues including the lesion, and vessels, etc., covered with blood due to bleeding are emphasized; therefore, it is possible to grasp the desired region of tissues such as the lesion and vessels which are covered with blood during surgery.

It is preferable to choose such light that has a wavelength difficult to be absorbed into blood (e.g. near-infrared light of 700 nm to 1000 nm) as the excitation light and the fluorescence.

Through this configuration, more of the excitation light can reach the tissues containing the fluorescence agent, and more of the fluorescence generated in the tissues can reach the endoscope.

Second Embodiment

The second embodiment of the present invention will be described, hereinafter.

In the aforementioned endoscopic device 100 according to the first embodiment, the corrected image generating section 43 adds to the G signal of each pixel in the correction target region of the white light image, thereby generating the corrected image a constant factor of the signal value of each corresponding pixel in the fluorescence image, but the present invention is not limited to this configuration; and for example, the corrected image generating section 43 may generate the corrected image by carrying out color conversion processing on each of the pixels of the white light image corresponding to the pixels each having luminance value equal to or more than the first threshold value in the fluorescence image.

Specifically, the corrected image generating section 43 compares the signal value of each pixel of the fluorescence image to the predefined first threshold value, and extracts pixels each having luminance value equal to or more than the predefined first threshold value, and defines as the correction target region a region constituted by pixels of the white light image corresponding to the pixels each having luminance value equal to or more than the first threshold value in the fluorescence image.

The correction target region of the white light image is multiplied by the following color conversion matrix so as to convert the correction target region in red with blood into green:

{Formula 1} where Or(i), Og(i), and Ob(i) represent respective signal values of the R, G, and B channels in the i-th pixel of the corrected image, Wr(i), Wg(i), and Wb(i) represents respective signal values of the R, G, and B channels in the i-th pixel of the white light image.

In this manner, the correction target region is multiplied by the color conversion matrix so as to convert the red color in the correction target region into another color; therefore, the correction target region, that is, the tissues including the lesion, and vessels, etc., covered with blood can be easily grasped by displaying this region in a different color from the blood color. In the case of multiplying the correction target region by the color conversion matrix, only the color of the pixels included in the correction target region can be changed while the contrast thereof is maintain. In the above formula 1, an example of converting the red color in the correction target region into the green color, but the present invention is not limited to this, and this may be changed into blue or the like, instead.

Third Embodiment

The third embodiment of the present invention will be described, hereinafter.

In the aforementioned endoscopic device 100 according to the first embodiment, the corrected image generating section 43 generates the corrected image such that the pixels of the white light image corresponding to the pixels each having luminance value equal to or more than the first threshold value in the fluorescence image are emphasized; but in the present embodiment, the corrected image generating section 43 generates the corrected image such that emphasized are the pixels of the white light image corresponding to pixels each having luminance value equal to or more than a second threshold value in a division image, which is generated by dividing the fluorescence image by the R signal of the white light image.

Figure 5:
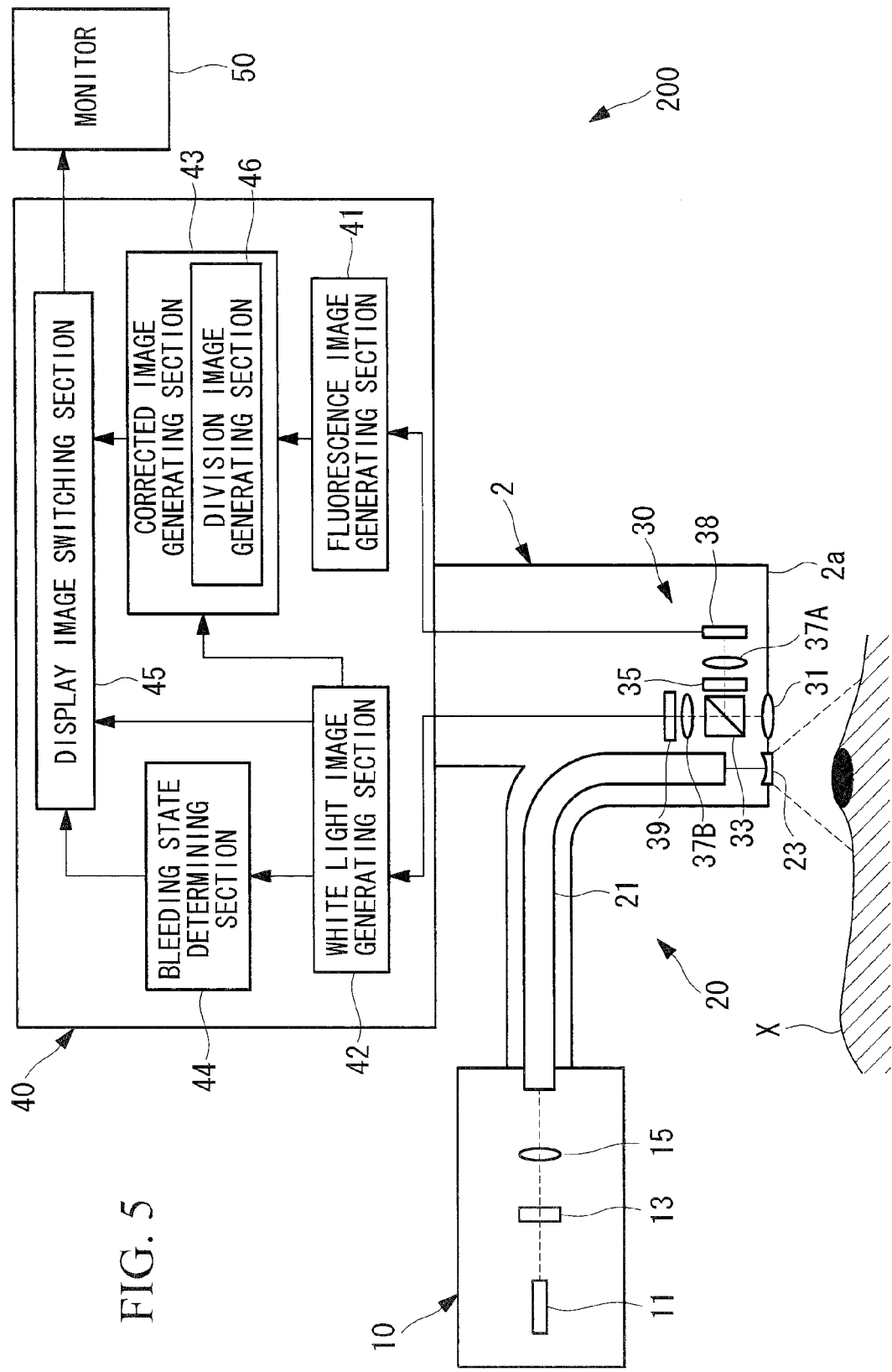
FIG. 5 is a schematic diagram of the endoscopic device according a variation of the third embodiment of the present invention.

Hence, as shown in FIG. 5, in the endoscopic device 200 according to the present variation, the corrected image generating section 43 includes a division image generating section 46 for generating a division image by dividing the fluorescence image by the white light image.

The division image generating section 46 generates the division image by dividing the fluorescence image inputted from the fluorescence image generating section 41 by the R signal of the white light image inputted from the white light image generating section 42. The corrected image generating section 43 compares the signal value of each pixel of the division image to the predetermined second threshold value, and extracts pixels each having luminance value equal to or more than the predefined second threshold value in the division image, and defines as the correction target region a region constituted by pixels of the white light image corresponding to the pixels each having luminance value equal to or more than the second threshold value in the division image.

As aforementioned in the first and second embodiments, the corrected image generating section 43 generates the corrected image by adding the signal value of each corresponding pixel in the fluorescence image (e.g. constant factor of luminance value) to the G channel of each pixel in the correction target region extracted based on the division image, or multiplying the correction target region by the color conversion matrix.

By dividing the fluorescence image by the R signal of the reference image in this manner, it is possible to generate the division image in which change in intensity of fluorescence depending on the observation distance and the observation angle is reduced while considering that the bleeding region is red. The corrected image is generated in which emphasized are the pixels of the white light image corresponding to the pixels each having luminance value equal to or more than the second threshold value of the division image; therefore, it is possible to more accurately grasp the desired tissue region including the lesion, and vessels, etc.

Fourth Embodiment

The fourth embodiment of the present invention will be described, hereinafter.

In the aforementioned first to third embodiments, the bleeding state determination is carried out on the entire treatment site X, that is, on the entire white light image. It is general, however, to carry out the treatment while displaying on the center of the monitor only a particular portion to be treated, such as the lesion of the treatment site X. In the present embodiment, an example of how the bleeding state determining section 44 determines the bleeding state on a predetermined area including the vicinity of the center of the white light image will be described with reference to a flow chart of FIG. 6. A center area of the display image except for portions of ¼ from the upper and lower edges and the left and right edges of this image may be exemplified as the predetermined area.

Figure 6:
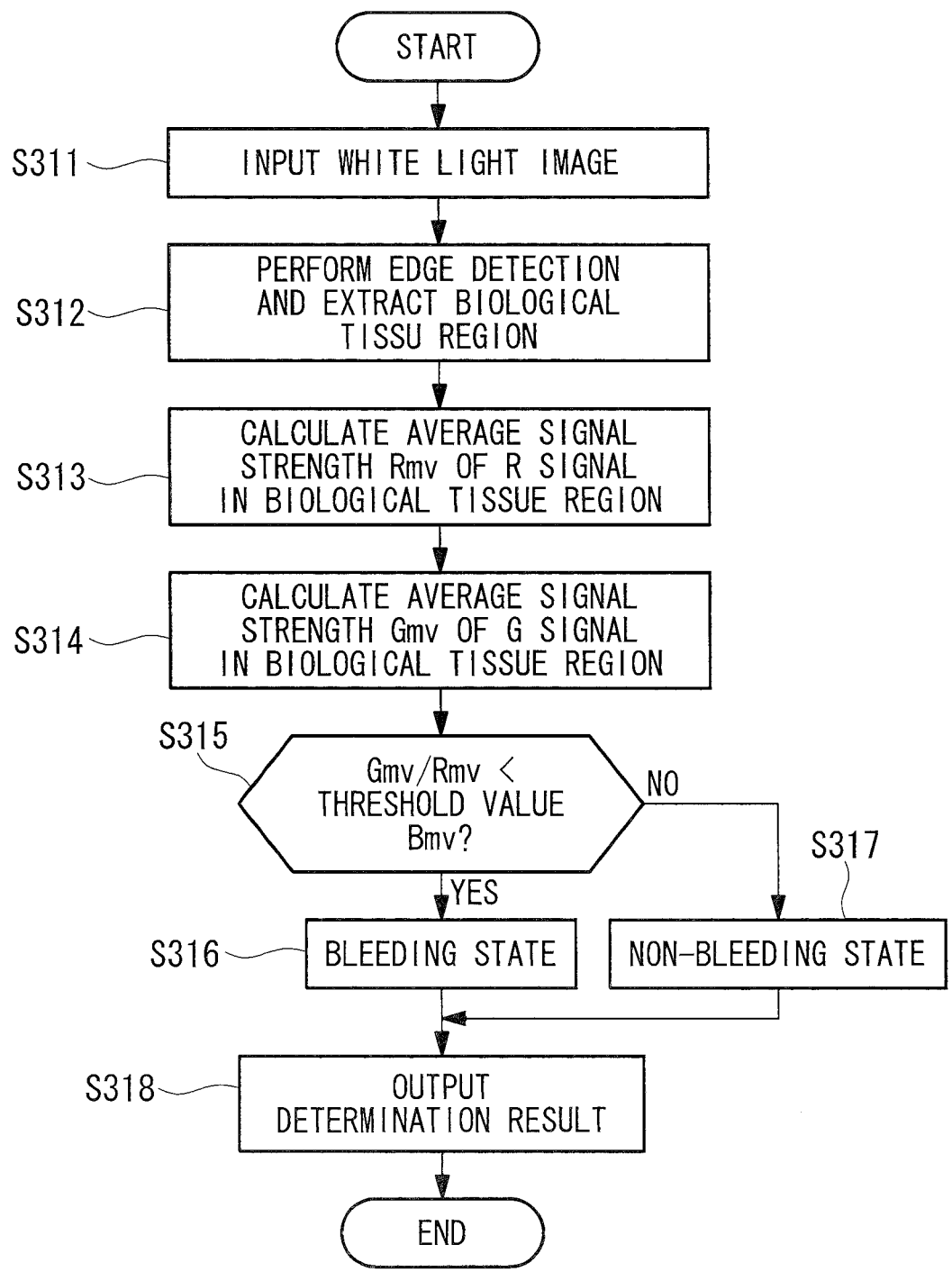
FIG. 6 is a flow chart of determining a bleeding state in the endoscopic device according a variation of the fourth embodiment of the present invention.

FIG. 6 shows a flow of how the bleeding state determining section 44 determines the bleeding state on the predetermined area including the vicinity of the center of the white light image. The bleeding state determining section 44 receives an input of the white light image generated by the white light image generating section 42 in step S311, detects the predefined bleeding determination region including the vicinity of the center portion, and also carries out an edge detection on the bleeding determination region in step S312. Forceps and others as treatment tools are placed at the portion to be treated including the lesion, the color and luminance value of the forceps are quite different from those of the biological tissues in the white light image. Hence, in step S312, the edge detection is carried out for the purpose of discriminating the bleeding determination region into a biological tissues region and a region other than the biological tissues. Subsequently, in step S313, an average signal value Rmv of the R signal among the all pixels in the biological tissue region is calculated, and in step S314, an average signal value Gmv of the G signal among the all pixels in the biological tissue region is calculated.

Subsequently, in step S315, the average signal value Rmv relative to the average signal value Gmv (Gmv/Rmv) is compared to a predetermined threshold value Bmv, and if the Gmv/Rmv value is equal to or more than the threshold value Bmv, it is determined that the concerned pixels are not corresponding to the bleeding state, and the process proceeds to step S317; and if the Gmv/Rmv value is less than the threshold value Bmv, it is determined that the concerned pixels are corresponding to the bleeding state, and the process proceeds to step S316.

This is because if the bleeding determination region is corresponding to the bleeding state, the Rmv value becomes increased, so that the Gmv/Rmv value also becomes decreased; and if the bleeding determination region is not corresponding to the bleeding state, the Rmv value becomes decreased, so that the Gmv/Rmv value also becomes increased. Accordingly, it can be determined that the bleeding determination region is corresponding to the bleeding state if the Gmv/Rmv value is smaller than the threshold value Bmv, and it can be determined that the bleeding determination region is not corresponding to the bleeding state if the Gmv/Rmv value is equal to or more than the threshold value Bmv. In step S318, one of the determination results: the bleeding state and the non-bleeding state is outputted to the display image switching section 45.

It is possible to reduce calculation cost in the image calculation as well as to reduce delay of the image display.

Fifth Embodiment

The fifth embodiment of the present invention will be described, hereinafter.

Figure 7:
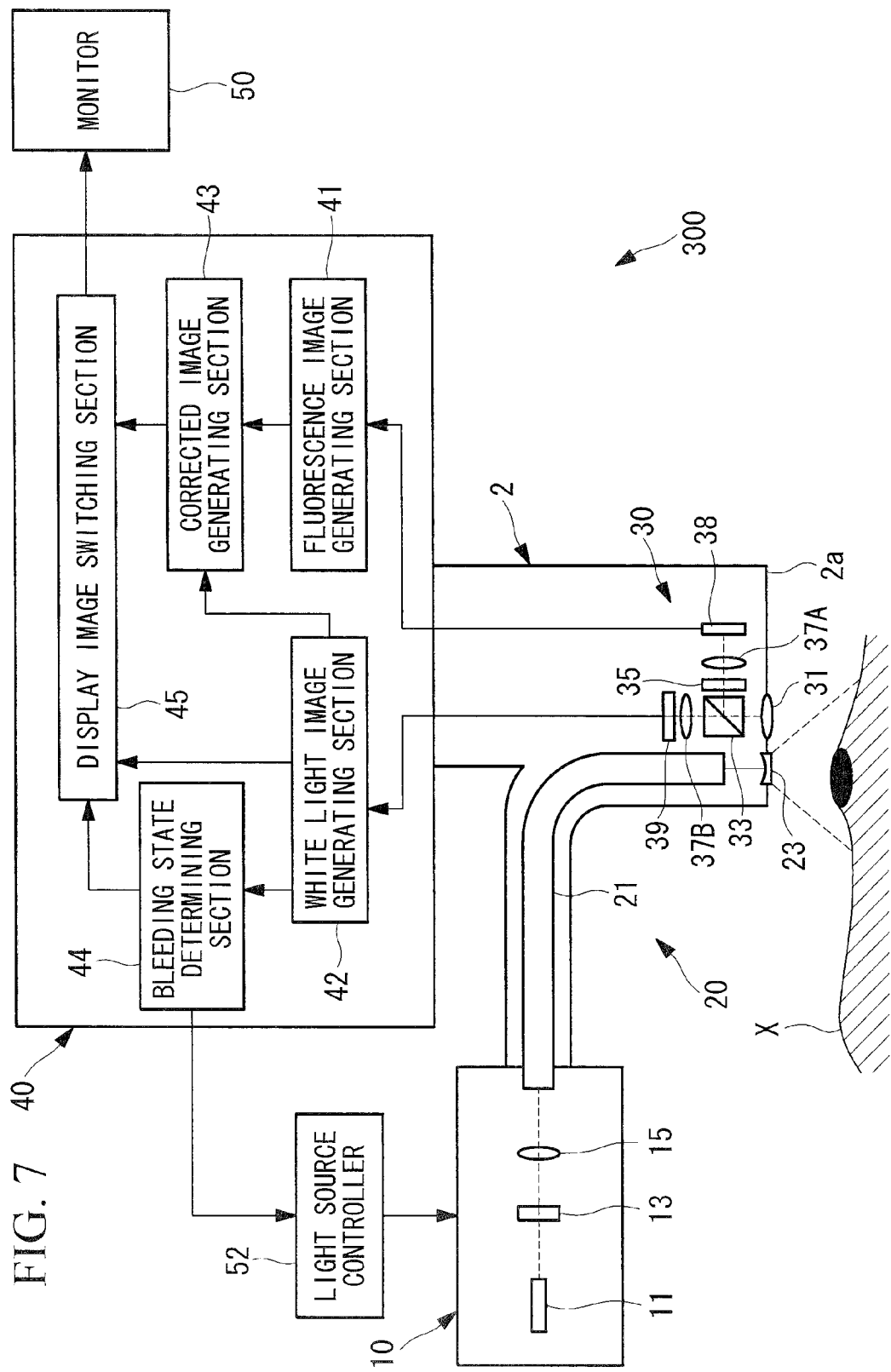
FIG. 7 is a schematic diagram of the endoscopic device according to the fifth embodiment of the present invention.

In order to acquire the fluorescence image, the fluorescence agent that is specifically accumulated in the lesion such as cancer cells is required to be applied or absorbed into the treatment site X prior to the treatment. In the case of a long-hour treatment or surgery, the fluorescence of the fluorescence agent becomes discolored due to continuous radiation of the excitation light. Hence, in the present embodiment, an endoscopic device 300 includes a light source controller 52 for controlling the light source 10, as shown in FIG. 7.

The light source controller 52 receives a determination result of the bleeding state from the bleeding state determining section 44, and if the received determination result is the bleeding state, the light source controller 52 outputs an instruction signal to the light controller 10 for radiating the excitation light. In this manner, if it is configured to radiate the excitation light only if necessary, which prevents discolor of fluorochrome; therefore, quality of the fluorescence image becomes hardly deteriorated due to the discolor, and it is possible to accurately grasp the desired tissue region such as the lesion and vessels in the corrected image.

The above embodiments have been described by using such an example that generates the corrected image in which the pixels of the white light image corresponding to the pixels each having predetermined luminance value or more in the fluorescence image are emphasized if it is determined to be corresponding to the bleeding state, but the present invention is not limited to this. For example, information regarding the bleeding state is outputted from the bleeding state determining section 44 so as to generate the corrected image in which emphasized are only the pixels that are included in the region determined to be corresponding to the bleeding state by the bleeding state determining section 44, and that are of the lesion or of the white light image corresponding to the pixels each having the predetermined luminance value or more in the fluorescence image. Through this configuration, it is possible to reduce time and computational complexity required for processing or calculating the generation of the corrected image, as well as to grasp the desired tissue region including the lesion, and vessels, etc.

The present embodiments have been described by exemplifying the endoscopic device, but the present invention is not limited to this, and the present invention may be applicable to any other fluorescence observation apparatus.

In endoscopic surgery using a conventional endoscopic device, if the lesion and the vicinity of the lesion are covered with blood due to bleeding, an image displayed on a monitor also includes a large red region of the lesion and the vicinity of the lesion covered with blood. Hence, once bleeding occurs, it may be difficult to grasp positions of biological tissues to be watched, such as the lesion, vessels, and nerves, which are a treatment object.

According to the above embodiments, when the subject is irradiated with the excitation light emitted from the light source, the fluorescence image is generated by the fluorescence image generating section based on the fluorescence generated in the subject, and when the subject is irradiated with the reference light emitted from the light source, the reference image is generated by the reference image generating section based on optical feedback of the reference light. The corrected image generating section generates the corrected image in which the pixels of the reference image, which are corresponding to the pixels of the fluorescence image each having luminance value equal to or more than the first threshold value, that is, the pixels having high luminance value resulting from strong fluorescence emitted from the lesion and the like of the subject, are emphasized. The bleeding determining section determines whether or not the bleeding region of the subject is more than the predetermined range based on the reference image. As a result, if it is determined that the bleeding region is not more than the predetermined range, the reference image is displayed on the image display unit, and if it is determined that the bleeding region is more than the predetermined range, the corrected image is displayed thereon.

If the bleeding region is not more than the predetermined range, observers such as doctors carry out the treatment while observing the reference image displayed on the image display unit; if the bleeding region is more than the predetermined range due to bleeding or the like during the treatment, the observes watch the corrected image displayed on the image display unit, which is switched from the reference image. Through this configuration, the pixels each having luminance value equal to or more than the first threshold value in the fluorescence image, that is, the corrected image in which the lesion or the like containing the fluorescence material especially accumulated is emphasized is displayed on the image display unit; thus it is possible to grasp the region including the lesion and others even if the tissues including the lesion, and vessels, etc., are covered with blood because of bleeding during the treatment.

In the above embodiments, preferably, the corrected image generating section generates the corrected image in which emphasized are pixels of the reference image included in the bleeding region detected by the bleeding state determining section, and corresponding to pixels each having a luminance value equal to or more than the first threshold value in the fluorescence image.

Even if the bleeding occurs during the surgery, the entire lesion and vessels are not always covered with blood; therefore, such a corrected image is generated in which emphasized are the pixels included in the bleeding region detected by the bleeding state determining section, and corresponding to the pixels each having luminance value equal to or more than the first threshold value in the fluorescence image, thereby reducing time and computational complexity required for the processing and the calculation, and also grasping the desired tissue region including the lesion, and vessels, etc.

In the above embodiments, preferably, the corrected image generating section adds to a predetermined color signal of each of the pixels of the reference image corresponding to the pixels each having a luminance value equal to or more than the first threshold value in the fluorescence image a signal value based on luminance value of each pixel having the luminance value equal to or more than the first threshold value in the fluorescence image, thereby generating the corrected image.

Through this configuration, it is possible to increase the signal value of the pixels corresponding to the lesion where strong fluorescence is emitted from the subject. As a result, it is possible to emphasize these pixels, and to accurately grasp the desired tissue region including the lesion, and vessels, etc., in the corrected image.

In the above embodiments, preferably, the corrected image generating section applies color conversion to the pixels of the reference image corresponding to the pixels each having the luminance value equal to or more than the first threshold value in the fluorescence image, thereby generating the corrected image.

Through this configuration, it is possible to emphasize the lesion and others where the strong fluorescence is emitted from the subject, thereby accurately grasping the region such as the lesion in the corrected image.

In the above embodiments, preferably, the corrected image generating section generates a division image by dividing the fluorescence image by an R signal of the reference image, and generates the corrected image in which emphasized are pixels of the reference image corresponding to pixels each having a luminance value equal to or more than a second threshold value in the division image.

By dividing the fluorescence image by the R signal of the reference image in this manner, it is possible to generate the division image in which change in intensity of fluorescence depending on the observation distance and the observation angle is reduced while considering that the bleeding region is red. The corrected image is generated in which emphasized are the pixels of the reference image corresponding to the pixels each having luminance value equal to or more than the second threshold value of the division image; therefore, it is possible to more accurately grasp the desired tissue region including the lesion, and vessels, etc.

In the above embodiments, preferably, the corrected image generating section generates the corrected image in which emphasized are pixels of the reference image included in the bleeding region detected by the bleeding state determining section, and corresponding to pixels each having a luminance value equal to or more than the second threshold value in the division image.

Even if the bleeding occurs during the surgery, the entire lesion and vessels are not always covered with blood; therefore, such a corrected image is generated in which emphasized are the pixels included in the bleeding region detected by the bleeding state determining section, and corresponding to the pixels each having luminance value equal to or more than the second threshold value in the division image, thereby reducing time and computational complexity required for the processing and the calculation, and also grasping the desired tissue region including the lesion, and vessels, etc.

In the above embodiments, preferably, the corrected image generating section adds to a predetermined color signal of each of the pixels of the reference image corresponding to the pixels each having a luminance value equal to or more than the second threshold value in the division image a signal value based on luminance value of each pixel having the luminance value equal to or more than the second threshold value in the division image, thereby generating the corrected image.

Through this configuration, it is possible to emphasize the lesion where the strong fluorescence is emitted from the subject, thereby accurately grasping the desired tissue region such as the lesion and vessels in the corrected image.

In the above embodiments, preferably, the corrected image generating section applies color conversion to the pixels of the reference image corresponding to pixels each having a luminance value equal to or more than the second threshold value in the division image, thereby generating the corrected image.

Through this configuration, it is possible to emphasize the lesion where the strong fluorescence is emitted from the subject, thereby accurately grasping the desired tissue region such as the lesion and vessels in the corrected image.

In the above embodiments, preferably, no excitation light is radiated if the bleeding state determining section determines that the bleeding region is not more than the predetermined range; and the excitation light is radiated if the bleeding state determining section determines that the bleeding region is more than the predetermined range.

Through this configuration, it is possible to prevent discolor of fluorochrome by radiating the excitation light only if it is determined that the bleeding region is more than the predetermined range. Specifically, if the excitation light is radiated for hours onto a portion to which the fluorescence agent is applied in advance for acquiring the fluorescence image, the fluorescence from the fluorescence agent becomes discolored during long-hour treatment or surgery. Hence, it is configured to radiate the excitation light if necessary, which prevents discolor of fluorochrome, and acquires a fluorescence image in high quality; thus it is possible to accurately grasp the desired tissue region, such as the lesion and vessels, in the corrected image.

In the above embodiments, preferably, the bleeding state determining section detects the bleeding region in a predetermined area including a vicinity of a center of the reference image, and determines whether or not the bleeding region is more than the predetermined range.

Through this configuration, while reducing time and computational complexity required for the processing and the calculation, it is possible to grasp the desired tissue region, such as the lesion and vessels. Generally, surgeons acquire the reference image such that a treatment site such as the lesion is displayed at the central of the display section. Even if bleeding occurs, the bleeding region may not be pertinent to the treatment, and may be located at an end portion of the reference image in some cases. Accordingly, it is configured to detect the bleeding region in the predetermined area including the vicinity of the center of the reference image, as well as to determine whether or not this bleeding region is more than the predetermined range, thereby reducing time and computational complexity required for the processing and the calculation.

In the above embodiments, the bleeding state determining section may compare a signal value of the R signal of each pixel in the reference image to a signal value of at least one of a G signal or a B signal of each pixel in the reference image, thereby detecting the bleeding region.

Through this configuration, it is possible to detect the red color that is a blood color, thereby accurately detecting the bleeding region.

According to the embodiments, it is possible to attain such an effect that grasps a desired tissue region including a lesion, and vessels, etc., in an acquired image even if bleeding occurs during surgery.

REFERENCE SIGNS LIST

10 Light source
41 Fluorescence image generating section
42 White light image generating section (Reference image generating section)
43 Corrected image generating section
44 Bleeding state determining section
45 Display image switching section
46 Division image generating section
50 Monitor (image display unit)
52 Light source controller
100 Endoscopic device (fluorescence observation apparatus)
200 Endoscopic device (fluorescence observation apparatus)
300 Endoscopic device (fluorescence observation apparatus)

The invention claimed is:

1. A fluorescence observation apparatus, comprising:
a light source for radiating excitation light and reference light onto a subject; and
a processor comprising hardware, the processor being configured to:
generate a fluorescence image by capturing fluorescence generated at the subject due to the irradiation with the light source;
photograph optical feedback returning from the subject irradiated with the reference light from the light source so as to generate a reference image;
generate a corrected image in which pixels of the reference image corresponding to pixels each having a luminance value equal to or more than a first threshold value are emphasized in the fluorescence image;
detect a bleeding region of the subject based on the reference image;
determine whether or not the bleeding region is more than a predetermined range;

display the reference image if the bleeding region is determined to not be more than the predetermined range; and display the corrected image if the bleeding region is determined to be more than the predetermined range; and an image display for displaying the reference image or the corrected image;

wherein the generating of the corrected image adds to a predetermined color signal of each of the pixels of the reference image corresponding to the pixels each having a luminance value equal to or more than the first threshold value in the fluorescence image a signal value based on luminance value of each pixel having the luminance value equal to or more than the first threshold value in the fluorescence image, thereby generating the corrected image.

2. A fluorescence observation apparatus comprising:

a light source for radiating excitation light and reference light onto a subject; and a processor comprising hardware, the processor being configured to:

generate a fluorescence image by capturing fluorescence generated at the subject due to the irradiation with the light source;

photograph optical feedback returning from the subject irradiated with the reference light from the light source so as to generate a reference image;

generate a corrected image in which pixels of the reference image corresponding to pixels each having a luminance value equal to or more than a first threshold value are emphasized in the fluorescence image;

detect a bleeding region of the subject based on the reference image;

determine whether or not the bleeding region is more than a predetermined range;

display the reference image if the bleeding region is determined to not be more than the predetermined range; and display the corrected image if the bleeding region is determined to be more than the predetermined range; and an image display for displaying the reference image or the corrected image;

wherein the light source radiates no excitation light if the bleeding state determining section determines that the bleeding region is not more than the predetermined range; and the light source radiates the excitation light if the bleeding region is determined to be more than the predetermined range.

3. A fluorescence observation apparatus comprising:

a light source for radiating excitation light and reference light onto a subject; and a processor comprising hardware, the processor being configured to:

generate a fluorescence image by capturing fluorescence generated at the subject due to the irradiation with the light source;

photograph optical feedback returning from the subject irradiated with the reference light from the light source so as to generate a reference image;

generate a corrected image in which pixels of the reference image corresponding to pixels each having a luminance value equal to or more than a first threshold value are emphasized in the fluorescence image;

detect a bleeding region of the subject based on the reference image;

determine whether or not the bleeding region is more than a predetermined range;

display the reference image if the bleeding region is determined to not be more than the predetermined range; and display the corrected image if the bleeding region is determined to be more than the predetermined range; and an image display for displaying the reference image or the corrected image;

wherein the detection of the bleeding region compares a signal value of the R signal of each pixel in the reference image to a signal value of at least one of a G signal or a B signal of each pixel in the reference image, thereby detecting the bleeding region.

* * * * *